(12) United States Patent
Erickson et al.

(10) Patent No.: US 8,262,719 B2
(45) Date of Patent: Sep. 11, 2012

(54) BRAIDED FLANGE BRANCH GRAFT FOR BRANCH VESSEL

(75) Inventors: David Erickson, Memphis, TN (US); Nasser Rafiee, Andover, MA (US); Nareak Douk, Lowell, MA (US); Jonathan Morris, Santa Rosa, CA (US); Curtis Hanson, San Diego, CA (US); Matthew Rust, Santa Rosa, CA (US); Sonny Yamasaki, Rohnert Park, CA (US); Prema Ganesan, Oakland, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 38 days.

(21) Appl. No.: 12/816,115

(22) Filed: Jun. 15, 2010

(65) Prior Publication Data

US 2010/0256726 A1     Oct. 7, 2010

Related U.S. Application Data

(62) Division of application No. 11/685,368, filed on Mar. 13, 2007, now abandoned.

(51) Int. Cl.
*A61F 2/84* (2006.01)
(52) U.S. Cl. ...... 623/1.11; 606/108; 623/1.15; 623/1.23
(58) Field of Classification Search .................. 606/108; 623/1.11, 1.23, 1.15
See application file for complete search history.

(56) References Cited

U.S. PATENT DOCUMENTS

| | | | |
|---|---|---|---|
| 5,626,587 A * | 5/1997 | Bishop et al. ................ 606/143 |
| 5,725,552 A | 3/1998 | Kotula et al. |
| 5,846,261 A | 12/1998 | Kotula et al. |
| 5,944,738 A | 8/1999 | Amplatz et al. |
| 6,083,257 A | 7/2000 | Taylor et al. |
| 6,210,338 B1 | 4/2001 | Afremove et al. |
| 6,241,678 B1 | 6/2001 | Afremove et al. |
| 6,334,864 B1 | 1/2002 | Amplatz et al. |
| 6,368,339 B1 | 4/2002 | Amplatz |
| 6,402,772 B1 | 6/2002 | Amplatz et al. |
| 6,428,565 B1 | 8/2002 | Wisselink |
| 6,447,531 B1 | 9/2002 | Amplatz |
| 6,451,048 B1 | 9/2002 | Berg et al. |
| 6,468,301 B1 | 10/2002 | Amplatz et al. |
| 6,468,303 B1 | 10/2002 | Amplatz et al. |
| 6,506,204 B2 | 1/2003 | Mazzocchi |
| 6,579,303 B2 | 6/2003 | Amplatz |
| 6,599,308 B2 | 7/2003 | Amplatz |

(Continued)

FOREIGN PATENT DOCUMENTS

DE     10338702     3/2005

(Continued)

*Primary Examiner* — Thomas J Sweet
*Assistant Examiner* — Matthew Schall

(57) ABSTRACT

A braided flange branch graft formed of a braided super elastic memory material includes a neck between an inner flange and an outer flange. The neck is positioned in a side opening in a sidewall of a main stent graft and the inner flange and outer flange are deployed on opposite sides of the sidewall. The inner flange and the outer flange have a diameter greater than a diameter of the side opening in the sidewall of the main stent graft. Thus, the sidewall of the main stent graft is sandwiched between the inner flange and the outer flange securely and simply mounting the braided flange branch graft to the main stent graft. The braided flange has a substantially unobstructed fluid communication passage therethrough. Further, when stretched into a substantially cylindrical shape for delivery, the braided flange branch graft has a small delivery profile and is extremely flexible.

18 Claims, 7 Drawing Sheets

U.S. PATENT DOCUMENTS

| | | |
|---|---|---|
| 6,638,257 B2 | 10/2003 | Amplatz |
| 6,682,546 B2 | 1/2004 | Amplatz |
| 6,827,736 B2 | 12/2004 | Perouse |
| 6,932,837 B2 | 8/2005 | Amplatz et al. |
| 7,001,409 B2 | 2/2006 | Amplatz |
| 2002/0029061 A1 | 3/2002 | Amplatz et al. |
| 2002/0123759 A1 | 9/2002 | Amplatz |
| 2002/0198561 A1 | 12/2002 | Amplatz |
| 2002/0198585 A1 | 12/2002 | Wisselink |
| 2003/0023299 A1 | 1/2003 | Amplatz et al. |
| 2003/0167068 A1 | 9/2003 | Amplatz |
| 2003/0171772 A1 | 9/2003 | Amplatz |
| 2005/0228434 A1 | 10/2005 | Amplatz et al. |
| 2005/0288764 A1* | 12/2005 | Snow et al. .................. 623/1.11 |
| 2006/0155359 A1 | 7/2006 | Watson |

FOREIGN PATENT DOCUMENTS

| | | |
|---|---|---|
| EP | 1576929 | 9/2005 |
| EP | 1113751 | 3/2007 |
| FR | 2847155 | 5/2004 |
| WO | WO97/42878 | 11/1997 |
| WO | WO99/12478 | 3/1999 |
| WO | WO99/39646 | 8/1999 |
| WO | WO00/10452 | 3/2000 |
| WO | WO01/37894 | 5/2001 |
| WO | WO01/37897 | 5/2001 |
| WO | WO01/72240 | 10/2001 |
| WO | WO01/72367 | 10/2001 |
| WO | WO01/87163 | 11/2001 |
| WO | WO03/074119 | 9/2003 |

* cited by examiner

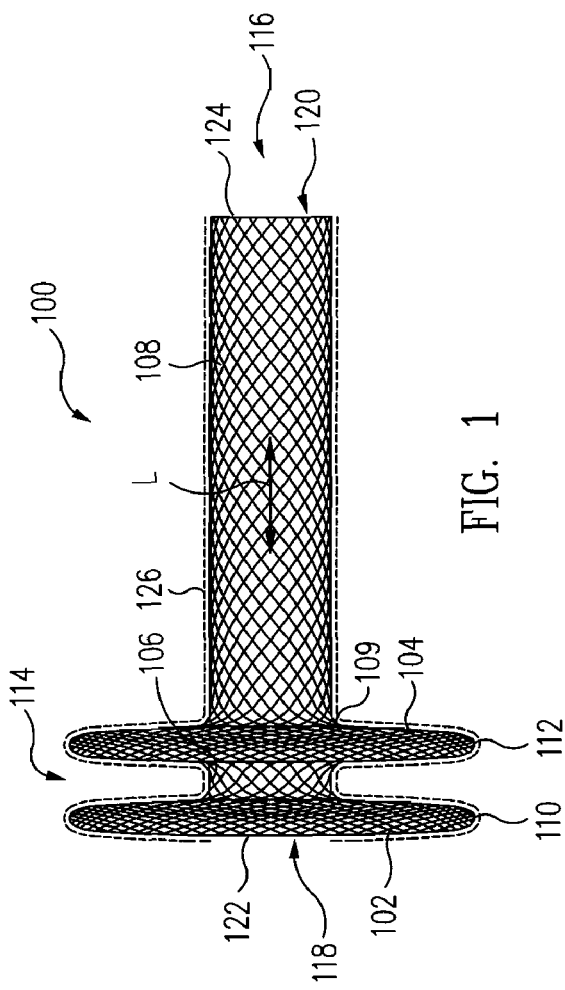
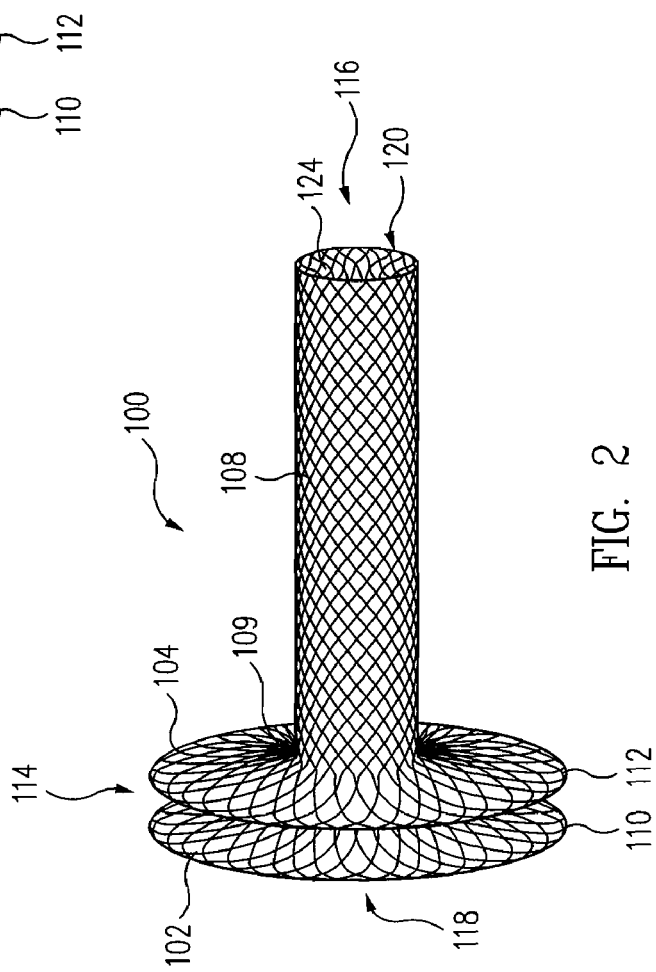

BRAIDED FLANGE BRANCH GRAFT FOR BRANCH VESSEL

RELATED APPLICATIONS

This application is a Divisional of and claims the benefit of U.S. patent application Ser. No. 11/685,368 filed Mar. 13, 2007. The disclosures of which is incorporated herein by reference in its entirety.

BACKGROUND OF THE INVENTION

1. Field of the Invention

The present invention relates to an intra-vascular device and method. More particularly, the present invention relates to a device used to treat aneurysms where a branch connection from a main stent graft crosses the ostium of a branch vessel.

2. Description of Related Art

A conventional main stent graft typically includes a radially expandable reinforcement structure, formed from a plurality of annular stent rings, and a cylindrically shaped layer of graft material defining a lumen to which the stent rings are coupled. Main stent grafts are well known for use in tubular shaped human vascular or other body vessel.

Endovascular aneurysmal exclusion is a method of using a main stent graft to partially or completely isolate an aneurysmal sac from systemic blood pressure by preventing pressurized blood flow from pressurizing the interior of an aneurysm, thereby reducing the risk of rupture of the aneurysm and the need for an invasive surgical intervention.

Illustratively, the main (body) stent graft was placed in the main vessel, e.g., the aorta, to exclude an aneurysm. A (branch) fenestration (opening) in the side of the main body provides an opening for blood flow to a branch vessel which would otherwise be obstructed by the position of the main body across the ostium of the branch vessel. A branch graft or branch stent graft was then inserted through the side opening and into the branch vessel spanning any gap between the outside of the branch opening in the main body and the ostium of the branch vessel, and carrying blood across the gap without pressuring the aneurysm.

Initially, the main stent graft was deployed in the main vessel such that an opening in the sidewall of the main stent graft was aligned with the branch vessel. A branch graft having a silicone flange was then passed through the opening in the main stent graft and deployed in the branch vessel. The silicone flange was configured to engage with and seal with the opening in the sidewall of the main stent graft. However, the silicone flange had a relatively large delivery profile and was somewhat inflexible thus limiting the range of applications in which the silicone flange with attached branch grafts could be used.

SUMMARY OF THE INVENTION

In accordance with one example, a braided flange branch graft formed of a braided super elastic memory material includes a neck between an inner flange and an outer flange. The neck is positioned in an opening in a sidewall of a main stent graft and the inner flange and outer flange are deployed on opposite sides of the sidewall.

The inner flange and the outer flange have a diameter greater than a diameter of the opening in the sidewall of the main stent graft. Thus, the sidewall of the main stent graft is sandwiched between the inner flange and the outer flange securely and simply mounting the braided flange branch graft to the main stent graft. Further, when longitudinally stretched into a substantially cylindrical shape for delivery, the braided flange branch graft has a small delivery profile and is extremely flexible.

Embodiments are best understood by reference to the following detailed description when read in conjunction with the accompanying drawings.

BRIEF DESCRIPTION OF THE DRAWINGS

FIG. 1 is a side plan view of a braided flange branch graft in accordance with one embodiment;

FIG. 2 is a perspective view of the braided flange branch graft of FIG. 1;

Common reference numerals are used throughout the drawings and detailed description to indicate like elements.

DETAILED DESCRIPTION

Figure 7:
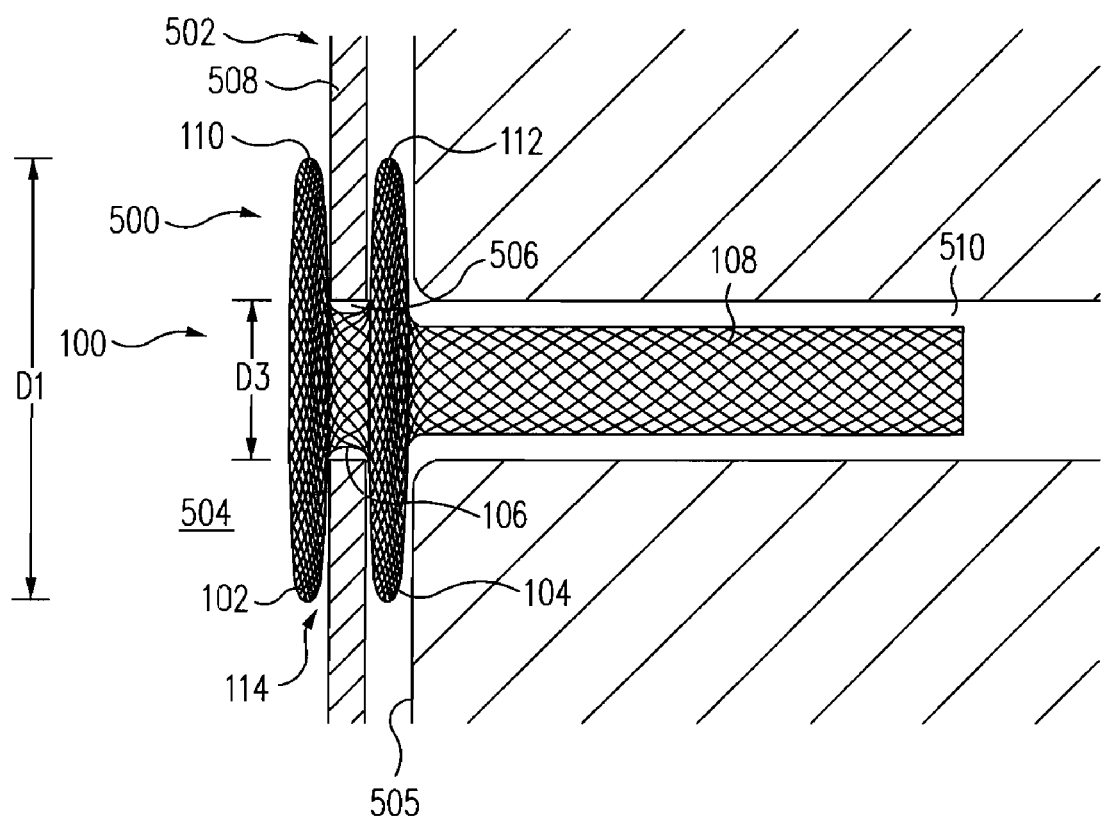

In accordance with one example, referring to FIG. 7, a braided flange branch graft 100 formed of a braided super elastic memory material (e.g., nitinol) includes a neck 106 between an inner flange 102 and an outer flange 104. Neck 106 is positioned in a side opening 506 in a sidewall 508 of a main stent graft 502 and inner flange 102 and outer flange 104 are deployed on opposite sides of sidewall 508. Inner flange 102 and outer flange 104 have a diameter D1 greater than a diameter D3 of side opening 506. Thus, sidewall 508 of main stent graft 502 is sandwiched between inner flange 102 and outer flange 104 securely and simply mounting braided flange branch graft 100 to main stent graft 502. Further, referring to FIG. 5, when stretched into a substantially cylindrical shape for delivery, braided flange branch graft 100 has a small delivery profile and is extremely flexible.

Figure 3:
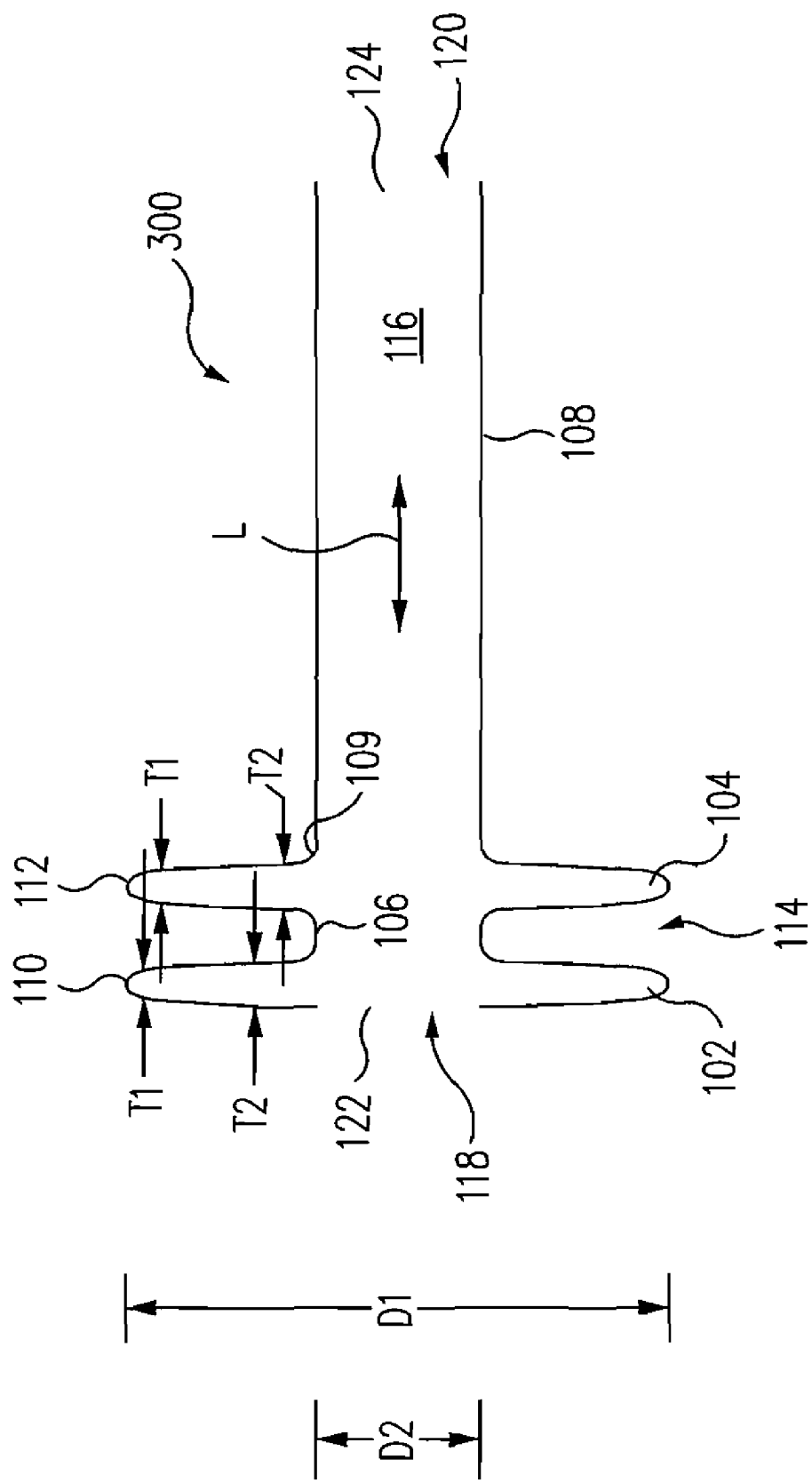
FIG. 3 is a cross-sectional view outline of the braided flange branch graft corresponding to the side plan view of FIG. 1.

More particularly, FIG. 1 is a side plan view of a braided flange branch graft 100, sometimes called a side branch, in accordance with one embodiment. FIG. 2 is a perspective view of braided flange branch graft 100 of FIG. 1. FIG. 3 is a cross-sectional view outline 300 of braided flange branch graft 100 corresponding to the side plan view of FIG. 1.

Referring now to FIGS. 1, 2 and 3 together, braided flange branch graft 100 has a longitudinal axis L. As used herein, longitudinally means in a direction parallel to longitudinal axis L. Radially means in a direction perpendicular to longitudinal axis.

Braided flange branch graft 100 includes an inner, e.g., first, flange 102, and an outer, e.g., second, flange 104, a neck 106, and a trunk 108.

Neck 106 is longitudinal between inner flange 102 and outer flange 104. Inner flange 102 and outer flange 104 extend radially outward from neck 106. More particularly, inner flange 102 and outer flange 104 have a first diameter D1 at outer radial perimeters 110, 112, respectively, greater than a second diameter D2 of neck 106. Accordingly, inner flange 102, outer flange 104, and neck 106 collectively define an annular channel 114.

Inner flange 102, sometimes called an inner disk, is saucer shaped in accordance with this example. More particularly, outer radial perimeter 110 of inner flange 102 is circular. Further, the thickness of inner flange 102 increases towards the radial center of inner flange 102. To illustrate, a first thickness T1 of inner flange 102 at outer radial perimeter 110 is less than a second thickness T2 of inner flange 102 at the point where inner flange 102 meets neck 106.

Similarly, outer flange 104, sometimes called an outer disk, is saucer shaped in accordance with this example. More particularly, outer radial perimeter 112 of outer flange 104 is circular. Further, the thickness of outer flange 104 increases towards the radial center of outer flange 104. To illustrate, a first thickness T1 of outer flange 104 at outer radial perimeter 112 is less than a second thickness T2 of outer flange 104 at the point where outer flange 104 meet neck 106.

Although inner flange 102 and outer flange 104 are described and illustrated as being saucer shaped, i.e., being in the shape of a disk that increases in thickness towards the radial center of the disk, in other examples, inner flange 102 and outer flange 104 are in the shape of a uniform thickness disk.

Trunk 108 extends longitudinally outward from outer flange 104 in a direction opposite inner flange 102. Trunk 108 includes a base 109 attached to outer flange 104. In accordance with this example, trunk 108 is cylindrically shaped, the cylinder having longitudinal axis L.

Extending longitudinally through braided flange branch graft 100 is a lumen 116. More particularly, braided flange branch graft 100 includes an inner end 118, e.g., a first longitudinal or proximal end, and an outer end 120, e.g., a second longitudinal or distal end. An inner, e.g., first, opening 122 of lumen 116 is formed in the radial center of inner flange 102 at inner end 118. A second opening 124 of lumen 116 is formed by the open end of trunk 108 at outer end 120. As set forth further below, fluid, e.g., blood, passes through lumen 116, e.g., from a main vessel into a branch vessel.

Braided flange branch graft 100 is formed of a braided super elastic memory material, e.g., nitinol, in accordance with one example. Generally, a super elastic memory material is a memory material that can be stretched from the shape of braided flange branch graft 100 shown in FIGS. 1 and 2 into a cylinder (see braided flange branch graft 100 of FIG. 5 for example) without permanent deformation of the memory material, i.e., the memory material will return from the cylinder to the shape of braided flange branch graft 100 shown in FIGS. 1 and 2 upon being released. A memory material is a material that can be set to have a specific shape, e.g., by heat setting, such that the material will return to the specific shape when the material is in its relaxed state.

Illustratively, the braid is made by intertwining strands of super elastic memory material, e.g., strands of nitinol. The strands are all of one type, e.g., nitinol, in one example.

In another example, two or more different types of strands are braided together to form braided flange branch graft 100. Illustratively, strands of a biocompatible polymer, e.g., polyester (PE) or polyester terephthalate (PET), are braided together with strands of a memory metal, e.g., nitinol, to form braided flange branch graft 100. For example, the biocompatible polymer encourages ingrowth of the surrounding body tissue into braided flange branch graft 100.

Illustratively, braided flange branch graft 100 is formed by heat setting a braided super elastic memory material. For example, a cylindrical shaped braid is forced over a mandrel having the shape of braided flange branch graft 100. In one example, the braid is clamped to the mandrel, for example, at neck 106, to ensure conformity with the mandrel. The assembly is then heat set using a conventional technique. In one embodiment the ends of braided flange branch graft 100 are fused, crimped, folded, or otherwise prevented from unravelling.

As discussed further below, braided flange branch graft 100 is stretched into a substantially cylindrical shape. Upon being released, braided flange branch graft 100 returns to its relaxed state as illustrated in FIGS. 1 and 2.

In another example, referring now to FIG. 1, braided flange branch graft 100 includes an elastic cover 126 illustrated by the dashed line. Illustratively, cover 126 is a super elastic material that conforms to the stretched and relaxed shape of the braided super elastic memory material of braided flange branch graft 100. Illustratively, cover 126 is elastic polytetrafluoroethylene (PTFE) over a nitinol braid.

Figure 4:
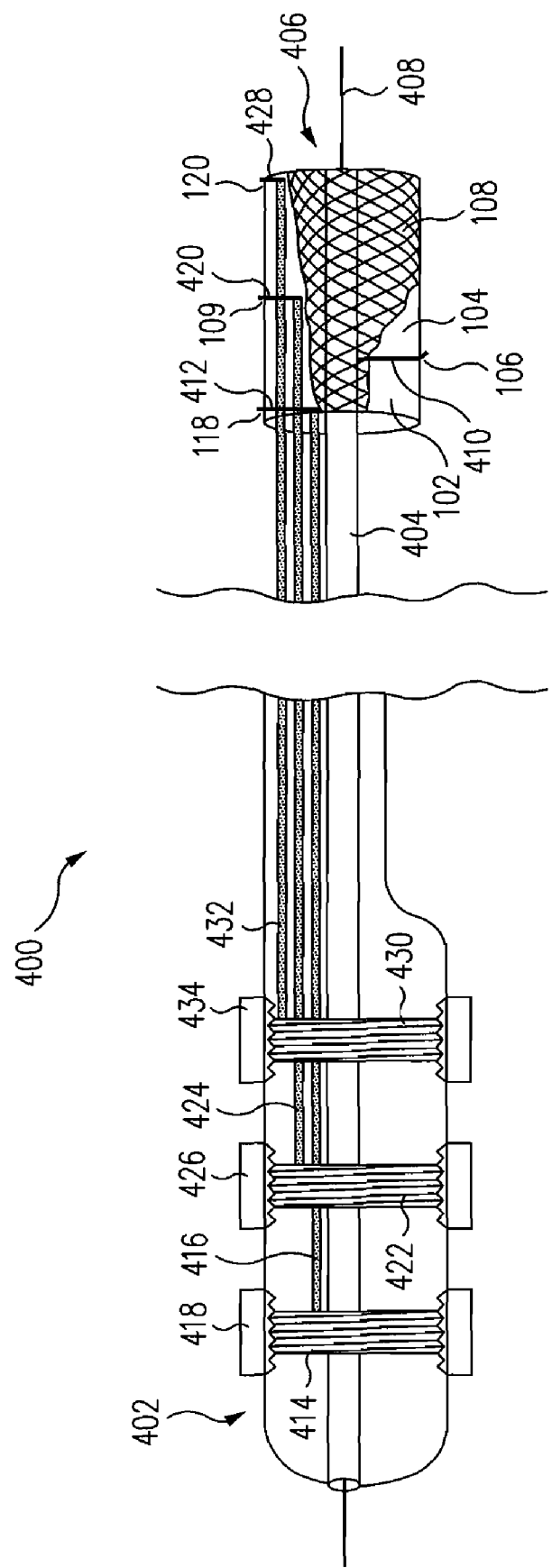
FIG. 4 is a cut away cross-sectional view of a braided flange branch graft delivery system for delivering the braided flange branch graft of FIGS. 1 and 2 into the vasculature of a patient.

FIG. 4 is a cross-sectional view of a braided flange branch graft delivery system 400 for delivering braided flange branch graft 100 of FIGS. 1 and 2 into the vasculature of a patient. Referring now to FIG. 4, delivery system 400 includes a handle 402. An inner member 404 extends distally from handle 402. Braided flange branch graft 100 is located over a distal end 406 of inner member 404. Braided flange branch graft 100 is partially cutaway in the view of FIG. 4 for clarity of presentation. As used herein, the proximal end of delivery system 400 is referenced with respect to the operator's handle, i.e., handle 402, while the proximal end of braided flange branch graft 100 is referenced with respect to the end closest to the heart via the length of blood traveled from the heart. (In this example the distal and proximal ends of each coincide.)

Inner member 404 is a hollow tubular member and includes a guide wire lumen. A guide wire 408 extends through the guide wire lumen of inner member 404.

Braided flange branch graft 100 is stretched into a substantially cylindrical shape by delivery system 400 to minimize the delivery profile of braided flange branch graft 100. Further, braided flange branch graft 100 is extremely flexible once stretched. Since braided flange branch graft 100 has a small delivery profile and is extremely flexible, braided flange branch graft 100 can be used in a wide variety of applications.

In accordance with this example, braided flange branch graft 100 is connected and stretched at inner end 118, neck 106, base 109, and outer end 120. More particularly, braided flange branch graft 100 is connected to a neck hook 410 at neck 106. Neck hook 410 is fixed in position and doesn't move relative to handle 402 in accordance with this example. Illustratively, neck hook 410 is mounted directly to inner member 404. After deployment of braided flange branch graft 100 as discussed further below, neck hook 410 is pulled from and releases braided flange branch graft 100 as inner member 404 is retracted.

Braided flange branch graft 100 is connected to an inner end hook 412 at inner end 118. Inner end hook 412 is connected to an inner end hook slider 414 of handle 402 by an inner end hook connector 416, e.g., a wire. Inner end hook slider 414 is threadedly connected to an inner end adjustment ring 418. Inner end adjustment ring 418 is rotated, e.g., by the physician, thereby causing longitudinal translation of inner end hook slider 414. More particularly, rotation of inner end adjustment ring 418 causes proximal or distal motion (left or right motion in the view of FIG. 4) of inner end hook slider 414 depending upon the direction of rotation of inner end adjustment ring 418.

Inner flange 102 is stretched into a cylindrical shape between inner end hook 412 and neck hook 410. Illustratively, inner end hook 412 is pulled proximally and towards handle 402 by inner end hook slider 414 through inner end hook connector 416. By rotating inner end adjustment ring 418, inner end hook slider 414 is moved distally towards braided flange branch graft 100. This releases the tension pulling on inner end hook 412. Inner end hook 412, in turn, releases the tension on braided flange branch graft 100 between inner end 118 and neck 106 thus allowing inner flange 102 to return to its relaxed shape, e.g., to the saucer shape of inner flange 102. While only a single set of hooks (one for each position) is shown in the Figures, multiple hooks and/or sets of hooks may be utilized in multiple radial directions to stabilize or distribute the forces at each axial (lateral) hook position with its respective braided engagement postion.

However, should the positioning of inner flange 102 be unsatisfactory, inner end adjustment ring 418 is rotated in the reverse direction. This causes inner end hook slider 414 to move proximally away from braided flange branch graft 100. This increases the tension pulling on inner end hook 412. Inner end hook 412, in turn, increases the tension on braided flange branch graft 100 between inner end 118 and neck 106 thus causing inner flange 102 to return to its stretched shape, e.g., to the cylindrical shape of inner flange 102 shown in FIG. 4. Braided flange branch graft 100 is then repositioned.

Once the positioning of inner flange 102 is satisfactory, continued distal travel of inner end hook 412 causes inner end hook 412 to slip from and release braided flange branch graft 100 thus permanently deploying inner flange 102.

Braided flange branch graft 100 is connected to a base hook 420 at base 109. Base hook 420 is connected to a base hook slider 422 of handle 402 by a base hook connector 424, e.g., a pair of coaxial hypo tubes. Base hook slider 422 is threadedly connected to a base adjustment ring 426.

Base adjustment ring 426 is rotated, e.g., by the physician, thereby causing longitudinal translation of base hook slider 422. More particularly, rotation of base adjustment ring 426 causes proximal or distal motion (left or right motion in the view of FIG. 4) of base hook slider 422 depending upon the direction of rotation of base adjustment ring 426.

Outer flange 104 is stretched into a cylindrical shape between base hook 420 and neck hook 410. Illustratively, base hook 420 is pushed distally and away from handle 402 by base hook slider 422 through base hook connector 424. By rotating base adjustment ring 426, base hook slider 422 is moved proximally away from braided flange branch graft 100. This releases the tension pushing on base hook 420. Base hook 420, in turn, releases the tension on braided flange branch graft 100 between base 109 and neck 106 thus allowing outer flange 104 to return to its relaxed shape, e.g., to the saucer shape of outer flange 104.

However, should the positioning of outer flange 104 be unsatisfactory, base adjustment ring 426 is rotated in the reverse direction. This causes base hook slider 422 to move distally towards braided flange branch graft 100. This increases the tension pushing on base hook 420. Base hook 420, in turn, increases the tension on braided flange branch graft 100 between base 109 and neck 106 thus causing outer flange 104 to return to its stretched shape, e.g., to the cylindrical shape of outer flange 104 shown in FIG. 4. Braided flange branch graft 100 is then repositioned.

Once the positioning of outer flange 104 is satisfactory, continued proximal travel of base hook 420 causes base hook 420 to slip from and release braided flange branch graft 100 thus permanently deploying outer flange 104.

Braided flange branch graft 100 is connected to an outer end hook 428 at outer end 120. Outer end hook 428 is connected to an outer end hook slider 430 of handle 402 by an outer end hook connector 432, e.g., a pair of coaxial hypo tubes. Outer end hook slider 430 is threadedly connected to an outer end adjustment ring 434.

Outer end adjustment ring 434 is rotated, e.g., by the physician, thereby causing longitudinal translation of outer end hook slider 430. More particularly, rotation of outer end adjustment ring 434 causes proximal or distal motion (left or right motion in the view of FIG. 4) of outer end hook slider 430 depending upon the direction of rotation of outer end adjustment ring 434.

Trunk 108 is stretched into an elongated cylindrical shape between outer end hook 428 and neck hook 410 (or base hook 420). Illustratively, outer end hook 428 is pushed distally and away from handle 402 by outer end hook slider 430 through outer end hook connector 432. By rotating outer end adjustment ring 434, outer end hook slider 430 is moved proximally away from braided flange branch graft 100. This releases the tension pushing on outer end hook 428. Outer end hook 428, in turn, releases the tension on braided flange branch graft 100 thus allowing trunk 108 to return to its relaxed shape, e.g., to a shorter greater diameter cylinder.

However, should the positioning of trunk 108 be unsatisfactory, outer end adjustment ring 434 is rotated in the reverse direction. This causes outer end hook slider 430 to move distally towards braided flange branch graft 100. This increases the tension pushing on outer end hook 428. Outer end hook 428, in turn, increases the tension on braided flange branch graft 100 between outer end 120 and neck 106 (or base 109) thus causing trunk 108 to return to its stretched shape, e.g., to the elongated cylindrical shape of trunk 108 shown in FIG. 4. Braided flange branch graft 100 is then repositioned.

Once the positioning of trunk 108 is satisfactory, continued proximal travel of outer end hook 428 causes outer end hook 428 to slip from and release braided flange branch graft 100 thus permanently deploying trunk 108.

Although four points of attachment to braided flange branch graft 100 for controlled deployment are set forth above, in other examples, only two or three points of attachment are used. For example, only inner end hook 412 and outer end hook 428 are attached to braided flange branch graft 100 and braided flange branch graft 100 is stretched between inner end hook 412 and outer end hook 428.

In another example, only inner end hook 412, neck hook 410, and outer end hook 428 are attached to braided flange branch graft 100. In accordance at this example, braided flange branch graft 100 is stretched between inner end hook 412 and neck hook 410, and between neck hook 410 and outer end hook 428. Further, other connection means can be used other than hooks.

In yet another example, braided flange branch graft 100 is constrained within a sheath of a delivery system. Retraction of the sheath exposes braided flange branch graft 100, which self-expands and is permanently deployed.

Figure 5:
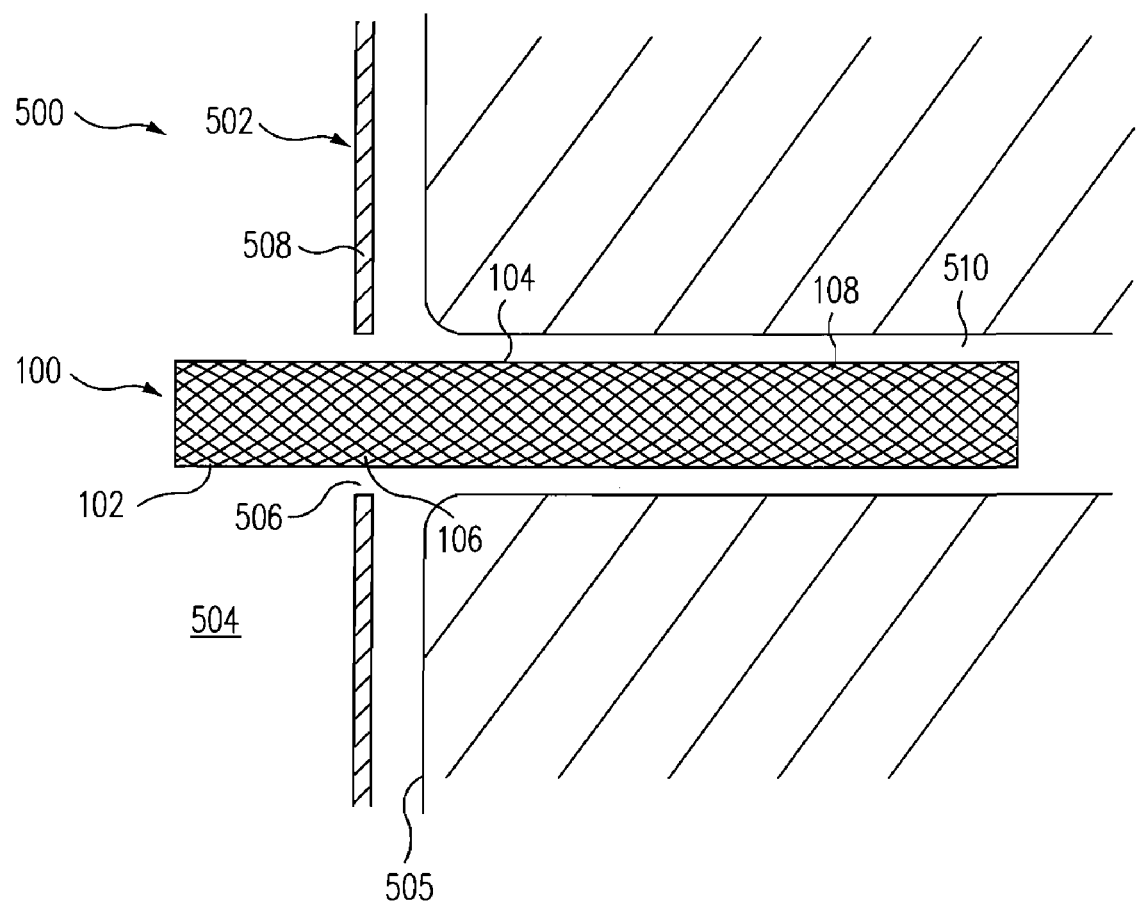
FIG. 5 is a cross-sectional view of a vessel system including the braided flange branch graft of FIGS. 1 and 2 in its stretched shape in accordance with one embodiment.

FIG. 5 is a cross-sectional view of a vessel system 500 including braided flange branch graft 100 of FIGS. 1 and 2 in its stretched shape in accordance with one embodiment. Referring now to FIG. 5, a main stent graft 502 is deployed within a main vessel 504 using any one of a number of techniques well known to those of skill in the art. Illustratively, main stent graft 502 is deployed to exclude an aneurysm in main vessel 504, main vessel 504 having a vessel wall 505.

A side opening 506 in a sidewall 508 of main stent graft 502 is aligned with a branch vessel 510 emanating from main vessel 504. Braided flange branch graft 100, in its stretched cylindrical shape, is inserted through side opening 506 and into branch vessel 510, for example, using delivery system 400 of FIG. 4. Since braided flange branch graft 100 has a small delivery profile and is extremely flexible, braided flange branch graft 100 can be used in a wide variety of applications, e.g., in the case when branch vessel 510 is small and difficult to reach.

Neck 106 of braided flange branch graft 100 is positioned within side opening 506 of main stent graft 502, for example, using a radiopaque marker or other imaging technique.

Figure 6:
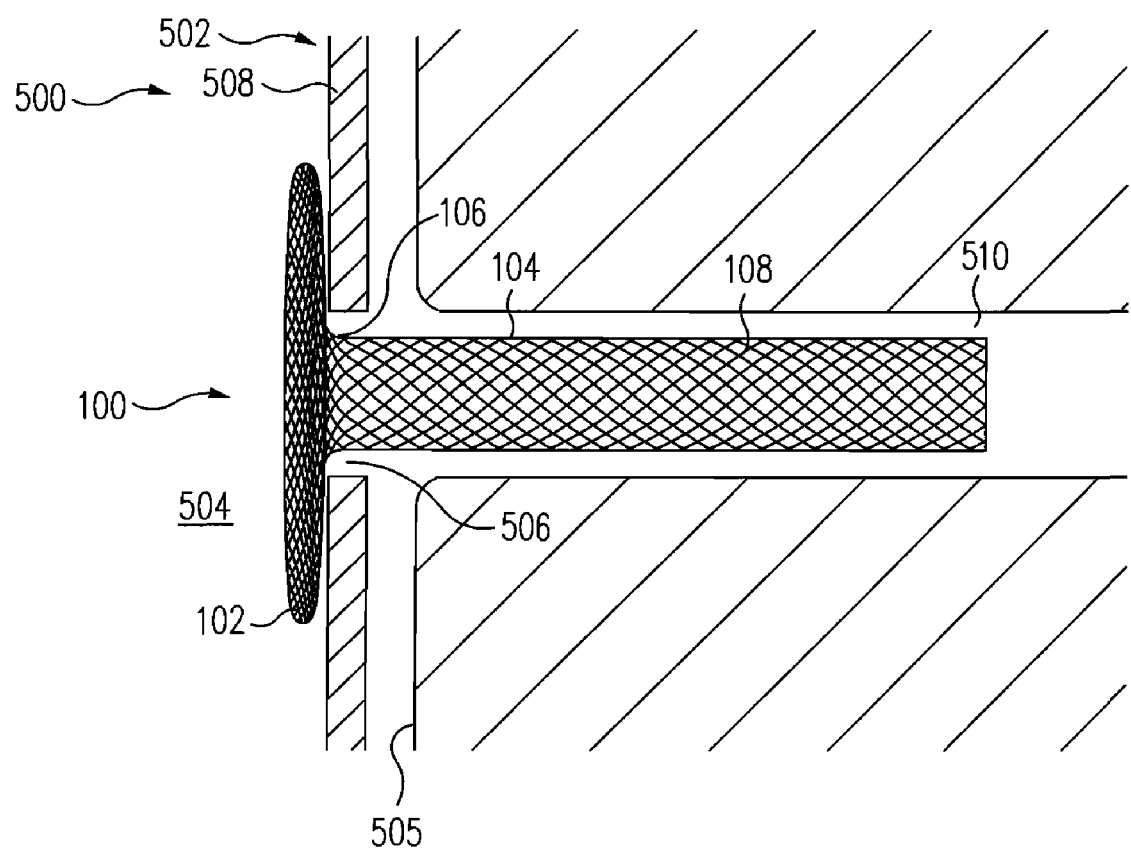
FIGS. 6, 7, 8 are cross-sectional views of the vessel system of FIG. 5 at further stages during deployment of the braided flange branch graft.

FIG. 6 is a cross-sectional view of vessel system 500 of FIG. 5 at a further stage during deployment of braided flange branch graft 100. Referring now to FIG. 6, inner flange 102 is deployed. More particularly, inner flange 102 is return to its relaxed shape, e.g., to its saucer shape, as shown in FIG. 6. Illustratively, inner flange 102 is deployed as discussed above in reference to delivery system 400 of FIG. 4. Inner flange 102 is deployed inside of main stent graft 502.

FIG. 7 is a cross-sectional view of vessel system 500 of FIG. 6 at a further stage during deployment of braided flange branch graft 100. Referring now to FIG. 7, outer flange 104 is deployed. More particularly, outer flange 104 is return to its relaxed shape, e.g., to its saucer shape, as shown in FIG. 7. Illustratively, outer flange 104 is deployed as discussed above in reference to delivery system 400 of FIG. 4. Outer flange 104 is deployed outside of main stent graft 502 and between main stent graft 502 and vessel wall 505.

As shown in FIG. 7, inner flange 102 and outer flange 104 are deployed on opposite sides of sidewall 508 of main stent graft 502. Further, inner flange 102 and outer flange 104 have a first diameter D1 at outer radial perimeters 110, 112, respectively, greater than a second diameter D3 of side opening 506. Thus, sidewall 508 of main stent graft 502 is sandwiched between inner flange 102 and outer flange 104 mounting and sealing braided flange branch graft 100 to main stent graft 502. In one example, both inner flange 102 and outer flange 104 push on sidewall 508 of main stent graft 502.

More particularly, sidewall 508 is located within annular channel 114 defined by inner flange 102, neck 106, and outer flange 104 of braided flange branch graft 100. Stated another way, inner flange 102, neck 106, and outer flange 104 form a locking mechanism, sometimes called a means for locking, for locking braided flange branch graft 100 to main stent graft 502.

In this manner, braided flange branch graft 100 is securely mounted to main stent graft 502 forming an intra-vascular assembly. The connection between braided flange branch graft 100 and main stent graft 502 is achieved by simply and reliably deploying inner flange 102 and outer flange 104 on opposite sides of sidewall 508 of main stent graft 502.

Figure 8:
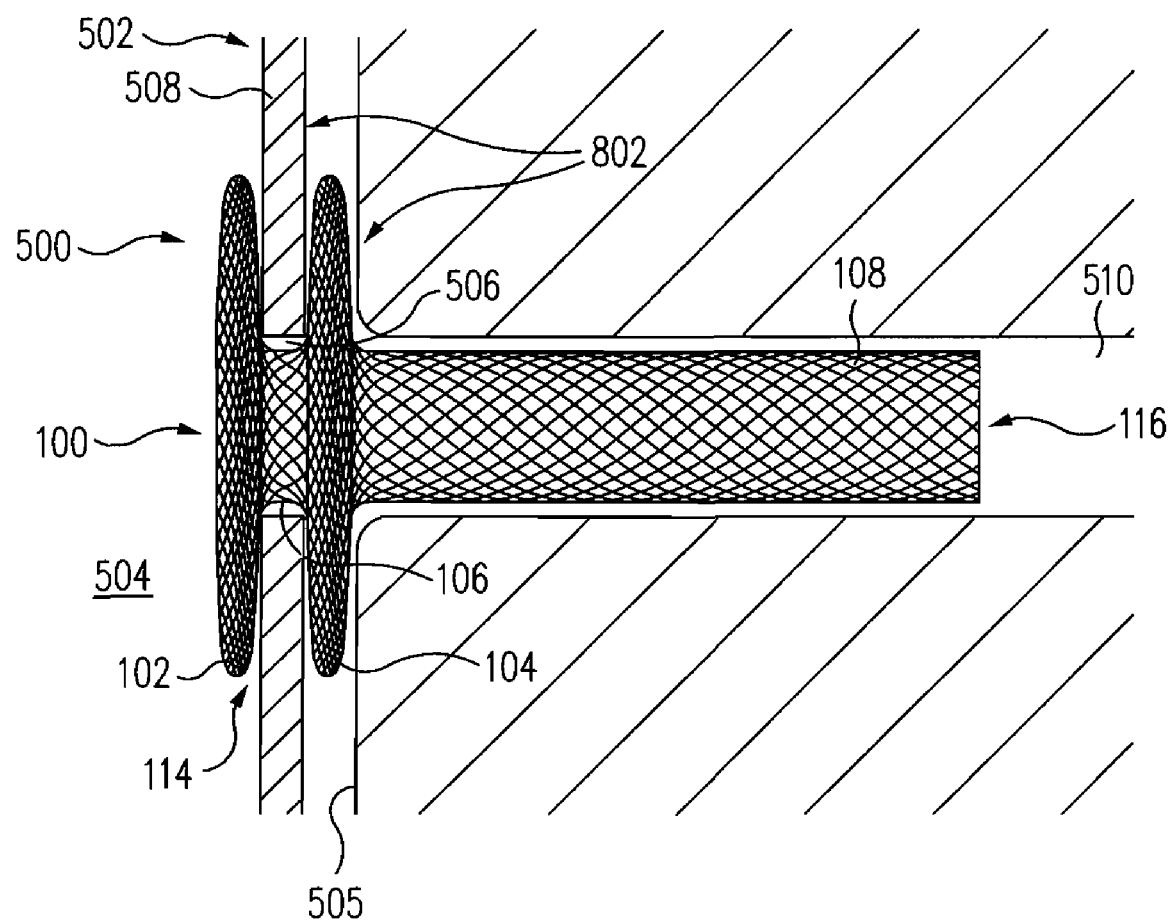

FIG. 8 is a cross-sectional view of vessel system 500 of FIG. 7 at a further stage during deployment of braided flange branch graft 100. Referring now to FIG. 8, trunk 108 is deployed. More particularly, trunk 108 is return to its relaxed shape, e.g., to its shorter larger diameter cylindrical shape, as shown in FIG. 8. Illustratively, trunk 108 is deployed as discussed above in reference to delivery system 400 of FIG. 4.

Trunk 108 is deployed inside of branch vessel 510. In one example, trunk 108 self-expands into branch vessel 510 to maintain patency of branch vessel 510. Once braided flange branch graft 100 is deployed, fluid, e.g., blood, passes through lumen 116 of braided flange branch graft 100, e.g., from the lumen defined by main stent graft 502 into branch vessel 510. More particularly, lumen 116 of braided flange branch graft 100 is in fluid communication with the lumen of main stent graft 502. Main stent graft 502 and braided flange branch graft 100 collectively form an intra-vascular assembly 802.

Although deployment of inner flange 102 before the deployment of outer flange 104 is set forth, in another example, outer flange 104 is initially deployed and then inner flange 102 is deployed. In yet another example, both inner flange 102 and outer flange 104 are deployed simultaneously.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A delivery system comprising:
    a braided flange branch graft formed from a braided super elastic memory material, said braided flange branch graft comprising:
        a first flange;
        a second flange;
        a neck between said first flange and said second flange; and
        a trunk extending longitudinally from said second flange, said braided flange branch graft being stretched into a substantially cylindrical shape;
    a handle;
    an inner member extending distally from said handle, said braided flange branch graft being located over a distal portion of said inner member;
    a neck hook connected to said neck of said braided flange branch graft;
    an inner end hook connected to an inner end of said braided flange branch graft, said inner end hook being longitudinally translatable relative to said neck hook, said first flange being stretched between said inner end hook and said neck hook; and
    a base hook connected to a base of said trunk, said base hook being longitudinally translatable relative to said neck hook, said second flange being stretched between said neck hook and said base hook.

2. The delivery system of claim 1 wherein said handle comprises:
    an inner end hook slider connected to said inner end hook by an inner end hook connector such that longitudinal translation of said inner end hook slider longitudinally translates said inner end hook via said inner end hook connector; and
    a base hook slider connected to said base hook by a base hook connector such that longitudinal translation of said base hook slider longitudinally translates said base hook via said base hook connector.

3. The delivery system of claim 2 wherein said handle further comprises:
    an inner end adjustment ring threadedly connected to said inner end hook slider such that rotation of said inner end adjustment ring longitudinally translates said inner end hook slider; and
    a base adjustment ring threadedly connected to said base hook slider such that rotation of said base adjustment ring longitudinally translates said base hook slider slider.

4. The delivery system of claim 2 wherein said inner end hook connector comprises a wire.

5. The delivery system of claim 2 wherein said base hook connector comprises a pair of coaxial hypo tubes.

6. The delivery system of claim 1 wherein said neck hook is connected to said inner member.

7. The delivery system of claim 1 wherein said inner member defines a guide wire lumen, said delivery system further comprising a guide wire in said guide wire lumen.

8. The delivery system of claim 1 further comprising an outer end hook connected to an outer end of said braided flange branch graft, said outer end hook being longitudinally translatable relative to said neck hook, said outer end hook stretching said trunk.

9. The delivery system of claim 8 wherein said handle comprises:
an outer end hook slider connected to said outer end hook by an outer end hook connector such that longitudinal translation of said outer end hook slider longitudinally translates said outer end hook via said outer end hook connector; and
an outer end adjustment ring threadedly connected to said outer end hook slider such that rotation of said outer end adjustment ring longitudinally translates said outer end hook slider.

10. A delivery system comprising:
a braided flange branch graft formed from a braided super elastic memory material, said braided flange branch graft having a delivery configuration and a deployed configuration, said braided flange branch graft comprising:
a first flange having a substantially saucer shape in the deployed configuration and a substantially cylindrical shape in the delivery configuration;
a second flange having a substantially saucer shape in the deployed configuration and a substantially cylindrical shape in the delivery configuration;
a neck between said first flange and said second flange; and
a trunk extending longitudinally from said second flange, said trunk having a substantially cylindrical shape in the deployed configuration and a substantially cylindrical shape with a reduced diameter and an increased length relative to the deployed configuration in the delivery configuration;
a handle;
an inner member extending distally from said handle, said braided flange branch graft being located over a distal portion of said inner member;
a neck hook connected to said neck of said braided flange branch graft;
an inner end hook connected to an inner end of said braided flange branch graft, said inner end hook being longitudinally translatable relative to said neck hook, wherein longitudinal translation of said inner end hook away from said neck hook stretches said first flange into the delivery configuration and wherein longitudinal translation of said inner end hook towards said neck hook converts said first flange from the delivery configuration to the deployed configuration; and
a base hook connected to a base of said trunk, said base hook being longitudinally translatable relative to said neck hook, wherein longitudinal translation of said base hook away from said neck hook stretches said second flange into the delivery configuration and wherein longitudinal translation of said base hook towards said neck hook converts said second flange from the delivery configuration to the deployed configuration.

11. The delivery system of claim 10 wherein said handle comprises:
an inner end hook slider connected to said inner end hook by an inner end hook connector such that longitudinal translation of said inner end hook slider longitudinally translates said inner end hook via said inner end hook connector; and
a base hook slider connected to said base hook by a base hook connector such that longitudinal translation of said base hook slider longitudinally translates said base hook via said base hook connector.

12. The delivery system of claim 11 wherein said handle further comprises:
an inner end adjustment ring threadedly connected to said inner end hook slider such that rotation of said inner end adjustment ring longitudinally translates said inner end hook slider; and
a base adjustment ring threadedly connected to said base hook slider such that rotation of said base adjustment ring longitudinally translates said base hook slider.

13. The delivery system of claim 11 wherein said inner end hook connector comprises a wire.

14. The delivery system of claim 11 wherein said base hook connector comprises a pair of coaxial hypo tubes.

15. The delivery system of claim 10 wherein said neck hook is fixedly connected to said inner member.

16. The delivery system of claim 10 wherein said inner member defines a guide wire lumen, said delivery system further comprising a guide wire in said guide wire lumen.

17. The delivery system of claim 10 further comprising an outer end hook connected to an outer end of said trunk, said outer end hook being longitudinally translatable relative to said neck hook, wherein longitudinal translation of said outer end hook away from said neck hook stretches said trunk into the delivery configuration and wherein longitudinal translation of said outer end hook towards said neck hook converts said trunk from the delivery configuration to the deployed configuration.

18. The delivery system of claim 17 wherein said handle comprises:
an outer end hook slider connected to said outer end hook by an outer end hook connector such that longitudinal translation of said outer end hook slider longitudinally translates said outer end hook via said outer end hook connector; and
an outer end adjustment ring threadedly connected to said outer end hook slider such that rotation of said outer end adjustment ring longitudinally translates said outer end hook slider.

* * * * *